ary Examiner—Richard Raymond

United States Patent [19]
Piccardi et al.

[11] 4,379,163
[45] Apr. 5, 1983

[54] PYRETHROIDS

[75] Inventors: Paolo Piccardi; Francesco Corda, both of Milan; Franco Gozzo, San Donato Milanese; Augusto Menconi; Angelo Longoni, both of Milan, all of Italy

[73] Assignee: Montedison, S.p.A., Milan, Italy

[21] Appl. No.: 273,541

[22] Filed: Jun. 15, 1981

Related U.S. Application Data

[63] Continuation of Ser. No. 15,105, Feb. 26, 1979, Pat. No. 4,328,237.

[30] Foreign Application Priority Data

Feb. 28, 1978 [IT] Italy .............................. 20713 A/78
Jan. 30, 1979 [IT] Italy .............................. 19703 A/79

[51] Int. Cl.³ .................... A01N 43/08; C07D 307/54
[52] U.S. Cl. ..................................... 424/285; 549/499
[58] Field of Search ........... 260/326 A, 326.43, 347.4, 260/465 D; 424/274, 275, 285, 304, 305; 549/65, 66, 72, 76, 77, 79, 499; 560/124

[56] References Cited

U.S. PATENT DOCUMENTS 4,183,948  1/1980  Huff ..................... 424/304
4,243,677  1/1981  Engel .................... 424/305
4,332,815  6/1982  Engel .................... 424/274

Primary Examiner—Richard Raymond
Attorney, Agent, or Firm—Morgan, Finnegan, Pine, Foley & Lee

[57] ABSTRACT

Pyrethroid type insecticides are described having the formula:

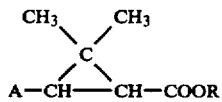

(I)

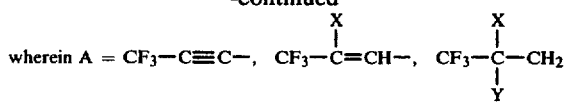

(X = H, F, Cl, Br; Y = Cl, Br)

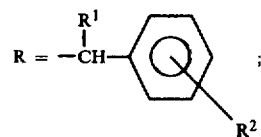

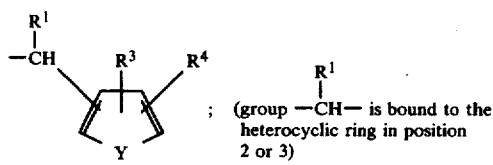

(group —CH— is bound to the heterocyclic ring in position 2 or 3)

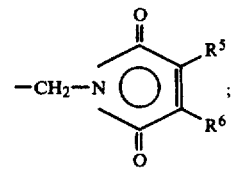

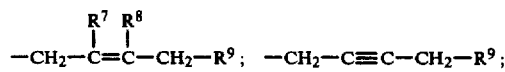

wherein:
$R^1$ = H, CN, C≡CH
$R^2$ = 3-phenoxy, 3-benzyl, 4-allyl, 4-propargyl.
$R^3$ = H, alkyl bound to the heterocyclic ring in position 3 or 2;
$R^4$ = (in position 4 or 5 of the heterocyclic ring) = benzyl, benzoyl, phenoxy, allyl, propargyl;
Y = O, S
$R^5$ and $R^6$ = alkyl $C_1$-$C_3$, or $R^5$ and $R^6$ together form an orthocondensed aromatic, heteroaromatic or aliphatic, saturated or unsaturated ring;
$R^7$ and $R^8$ (equal to or different from each other) = H, halogen, $CH_3$;
$R^9$ = phenyl, vinyl, vinyl substituted, phenoxy.

Compounds of general formula I are endowed with a high insecticide and acaricide activity.

7 Claims, No Drawings

PYRETHROIDS

This is a continuation of application Ser. No. 15,105, filed Feb. 26, 1979, now U.S. Pat. No. 4,328,237.

BACKGROUND OF THE INVENTION

Pyrethrines (or pyrethrum), that is esters of chrysanthemic acid (2,2-dimethyl-3-isobutenyl-cyclopropanecarboxylic) with a retronolone (2-alkenyl-3-methyl-cyclopent-2-en-4-olone), are insecticides of a natural origin whose characteristics are a rapid and high insecticide action coupled with a low toxicity for mammals.

Pyrethrum is, however, easily degradable by the action of the atmospheric agents and this behavior makes it unsuited for the protection of agricultural cultivations, limiting its use only to indoor application. Moreover, it is rather expensive, partly because of the complexity of the extraction processes and partly due to the necessity to couple it with suitable synergic substances.

In order to overcome these problems, a great number of substances with a structure similar to that of pyrethrum (pyrethroids) have been synthesized with the aim of preserving the insecticide action and the low toxicity for mammals while at the same time obtaining molecules that are more resistant to the action of the atmospheric agents (see for instance "Synthetic Pyrethroids (M. Elliott Ed.); ACS Symposium Series No. 42, Washington 1977").

Research has been directed towards the synthesis of new derivatives of 2,2-dimethyl-cyclopropanecarboxylic acid and of analogs, as well as towards the introduction of new groups, carrying alcoholic functions, to be esterified with the derivatives or the analogs of the 2,2-dimethylcyclopropanecarboxylic acids.

In the following Table 1 there are recorded a few of the pyrethroids that have shown interesting properties.

TABLE 1

| Common Name | W | Z | Bibliographical source |
|---|---|---|---|
| Pyrethrin I | 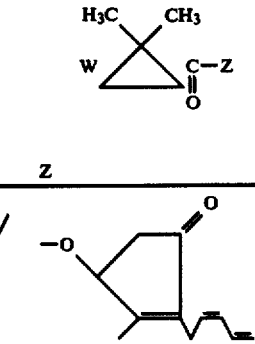 |  | Natural origin |
| Allethrin | 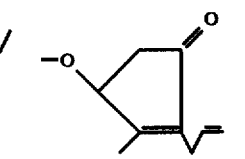 |  | Schechter et al. J.A.C.S 71, 3165 (1949) |
| Rosmethrin | 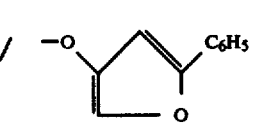 |  | Elliott et al., Nature (London), 213,493(1967) |
| Tetramethrin | 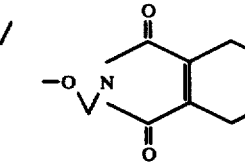 |  | Kato et al.,Agric.Biol. Chem. 28. 914 (1964) |
| Phenothrin | 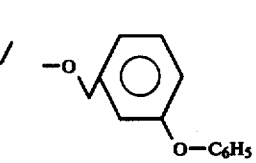 |  | Fujimoto et al.,Agric. Biol.Chem.,37.26S1(1973) |
| Permethrin | Cl, Cl | 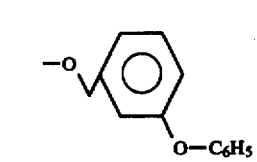 | M. Elliott et al.,Nature (London); 246. 169(1973) Pestic.Sci., 6.537(1975) |

TABLE 1-continued

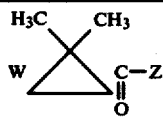

| Common Name | W | Z | Bibliographical source |
|---|---|---|---|
| Cypermethrin |  |  | M. Elliott - ACS Symposium Series n° 42 - Washington 1977 |
| Decamethrin |  | 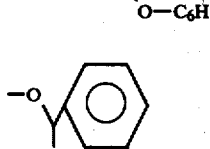 | M. Elliott - ACS Symposium Series n° 42 - Washington 1977 |

THE PRESENT INVENTION

We have now found, and they form an object of the present invention, new pyrethroids of general formula:

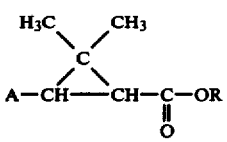

wherein A = $CF_3-C\equiv C-$, $CF_3-\overset{X}{\underset{}{C}}=CH-$, $CF_3-\overset{X}{\underset{Y}{C}}-CH_2$ (X = H, F, Cl, Br and Y = Cl, Br)

$R =$  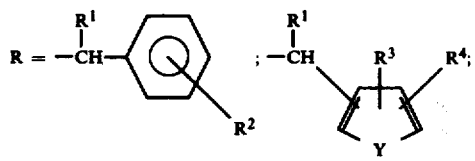

(the group $-\overset{R^1}{\underset{}{CH}}-$
is bound to the
heterocyclic ring
in position 2 or
3

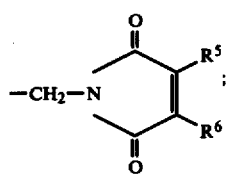

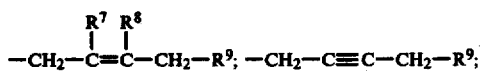

wherein
$R^1 = H$, CN, C≡CH
$R^2 = $ 3-phenoxy, 3-benzyl, 4-allyl, 4-propargyl $R^3 = H$, alkyl bound to the heterocyclic ring in position 3 or 2;
$R^4 = $ (in position 4 or 5 of the heterocyclic ring) = benzyl, benzoyl, phenoxy, allyl, propargyl;
$Y = O, S$
$R^5$ and $R^6 = $ alkyl $C_{1-3}$ or $R^5$ and $R^6$ together constitute an orthocondensed aromatic, heteroaromatic or aliphatic (saturated or unsaturated) ring;
$R^7$ and $R^8$ (equal to or different from each other) = H, halogen, $CH_3$
$R^9 = $ phenyl, vinyl, vinyl substituted, phenoxy.

The compounds of this invention are endowed with a high insecticide activity, greater than that of known synthetic pyrethroids having the same alcoholic structure.

The compounds of general formula (I) may be conveniently prepared by esterifying, by methods common to the practice of organic chemistry, the compounds of general formula:

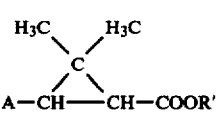

(wherein A has the meanings reported for the general formula I, and $R' = H$, lower alkyl), with R—OH alcohols (wherein R has the meanings given in general formula I).

For instance compounds of formula II may be converted into the corresponding acyl halides and these can be made to react with alcohols of formula R—OH in inert solvents and in the presence of an halogenhydric acid accepting base.

The compounds of general formula (II) have been described in the copending patent application filed concurrently herewith, corresponding to Italian application Ser. Nos. 20714 A/78 and 31310 A/78, filed Feb. 28, 1978 and Dec. 27, 1978, respectively.

Compounds of general formula (I), due to the presence of asymmetry centres and because of the possibility of cis, trans isomery, may occur as mixtures of isomers.

One peculiar characteristic of these mixtures is that they may be separated by simple means into geometrical isomers.

The separation of the mixtures into components thereof may be carried out by using known chemical methods such as for instance column chromatography or thin-layer chromatography.

It falls within the scope of this invention to isolate and use any steric and/or configurational isomer, as well as to directly use the mixtures obtainable from the preparation of the compounds and to use the mixtures derived from an incomplete separation of the isomers.

The compounds of this invention have shown, besides a very high activity against insects belonging to the most significant and important orders as for their noxiousness in the agricultural and civil fields, such as hemiptera, lepidoptera, coleoptera, diptera and blattoidea, also a satisfactory acaricide activity, definitely superior to that of many known pyrethroids.

The interest of the claimed compounds appears particularly evident when one considers the high level of insecticide activity found, together with the low acute toxicity, as appears respectively from the data reported in Table 2, wherein there appears a comparison with two known synthetic pyrethroids, an from Example 16.

The pyrethroids of this invention meet, moreover, the requirement of a good stability, as is shown in Example 17.

DESCRIPTION OF THE SPECIFIC EMBODIMENTS

In order to even better illustrate the inventive idea, a number of examples are given hereunder, of which Examples 1 to 14 relate to the synthesis of the pyrethroids of general formula I, using as starting product the 2,2-dimethyl-cyclopropanecarboxylic acids described in the copending patent application, corresponding to Italian application Ser. Nos. 20714 A/78 and 31310 A/78, filed Feb. 28, 1978 and Dec. 27, 1978, respectively.

EXAMPLE 1

Preparation of the m-phenoxybenzyl ester of (±)-cis,trans-2,2-dimethyl-3-(β-fluoro-β-trifluoromethyl-vinyl)-cyclopropanecarboxylic acid and partial separation of the geometrical isomers 9.5 g of 2,2-dimethyl-3-(β-fluoro-β-trifluoromethyl-vinyl)-cyclopropanecarboxylic acid were converted to the chloride of the acid by treatment with 9.7 g of PCl$_5$ in 200 ml of CCl$_4$ at 23°–24° C. By distillation under vacuum there were gathered 6.2 g of chloride of the acid. (Elemental analysis: found Cl=14.29% theoretical Cl=14.49%).

2.2 g of chloride of the acid thus obtained were esterified by treatment with 2.2 g of 3-phenoxybenzyl alcohol in 100 ml of anhydrous benzene, containing 2 ml of pyridine, at a temperature comprised between 18° and 24° C.

After filtering of the pyridinium salt, the solution was washed with 80 ml of an aqueous solution of HCl, then with water at 0° C. until attaining a neutral pH.

After dehydration, the solvent was evaporated under vacuum whereby there were obtained 4.1 g of raw 3-phenoxy-benzyl ester of the (±)-cis,trans-2,2-dimethyl-3-(β-fluoro,β-trifluoromethyl-vinyl)-cyclopropanecarboxylic acid.

In order to achieve a partial separation of the geometrical isomers, the product thus obtained was chromatographed on a silica gel column (Filler: silica gel Kieselgel G (Type 60) produced by Merck and analogous product by C. Erba code. 453332, in a weight ratio of 1:2, length of column=20 cm, diameter of column=2.4 cm; eluent: n-hexane-benzene (2:1), at room temperature), gathering the following fractions:

Fraction I: sample 1-A (1 g)
Fraction II: sample 1-M (0.6 g)
Fraction III: sample 1-B (1.2).

On the basis of Nuclear Magnetic Resonance (NMR) analysis, sample 1-A proved to consist predominantly (at least 90%) of the isomer 3-phenoxybenzyl-ester of (±)-cis-2,2-dimethyl-3-(β-fluoro,β-trifluoromethyl(E)-vinyl)cyclopropanecarboxylic acid.

Sample 1-B proved to consist predominantly (at least 80%) of the isomer 3-phenoxybenzyl ester of (±)-trans-2,2-dimethyl-3-(β-fluoro,β-trifluoromethyl(E)vinyl)cyclopropanecarboxylic acid.

Sample 1-M proved to consist of a mixture of the two above indicated isomers in a cis:trans ratio of about 1:3.

The characteristics of these samples have been rcorded herebelow.

| | NMR (δ, ppm) |
|---|---|
| 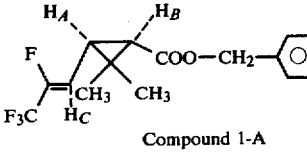<br>Compound 1-A | 2 (m, H$_A$ + H$_B$)<br>6.1 (dd, H$_C$)<br>1.23 (s, geminal methyls)<br>5.06 (s, CH$_2$)<br>6.8–7.5 (m, aromatic protons)<br>J (H$_C$, F trans) = 33 Hz<br>J (H$_C$, H$_A$) = 9 Hz |
| 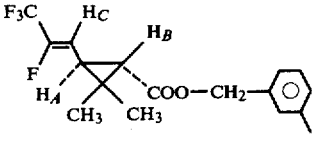<br>Compound 1-B | 1.7 (d, H$_B$)<br>2.33 (dd, H$_A$)<br>5.23 (dd, H$_C$)<br>1.16 (s, CH$_3$)<br>1.25 (s, CH$_3$)<br>5.05 (s, CH$_2$)<br>6.8–7.4 (m, aromatic protons)<br>J (H$_C$, H$_A$) = 9 Hz<br>J (H$_A$, H$_B$) = 5 Hz<br>J (H$_C$, F trans) = 31 Hz |

*s = singlet; d = doublet; dd = doublet of doublet; m = multiplet; J = coupling constant

EXAMPLE 2

Preparation of the 2-methyl-5-benzyl-3-furylmethyl ester of the (±)-cis,trans-2,2-dimethyl-3-(β-fluoro-β-trifluoromethyl-vinyl)cyclopropanecarboxylic acid and separation of the geometrical isomers The above indicated compound was obtained according to a process similar to that described in Example 1, starting from 2.2 g of chloride of 2,2-dimethyl-3-(β-fluoro-β-trifluoromethyl-vinyl)-cyclopropanecarboxylic acid and from 2.3 g of 2-methyl-5-benzyl-3-furylmethyl alcohol.

After an analogous processing there were obtained 4.3 g of raw 2-methyl-5-benzyl-3-furyl-methyl ester of (±)-cis,trans-2,2-dimethyl-3-(β-fluoro,β-trifluoromethyl(E)vinyl)cyclopropanecarboxylic acid (NMR consistent with the structure).

By chromatography on a silica gel column, under the same conditions described in Example 1, the raw ester was resolved into two geometrical isomers:
Fraction I: sample 2 A (0.7 g) (cis)
Fraction II: sample 2 B (1.8 g) (trans).

On the basis of the nuclear magnetic resonance analysis (NMR) sample 2 A proved to consist predominantly (≧90%) of the isomer 2-methyl-5-benzyl-3-furyl-methyl ester of (±)-cis-2,2-dimethyl-3-(β-fluoroβ-trifluoromethyl(E)vinyl)cyclopropanecarboxylic acid.

Sample 2 B proved to consist predominantly (≧90%) of the isomer 2-methyl-5-benzyl-3-furyl-methyl ester of (±)-trans-2,2-dimethyl-3-(β-fluoro-β-trifluoromethyl-(E)vinyl)cyclopropanecarboxylic acid.

The NMR data of samples 2A and 2B have been recorded herebelow.

EXAMPLE 3

By a process analogous to that described in Example 1, starting from 2,2-dimethyl-3-β-fluoro-β-trifluoromethyl-vinyl)-cyclopropanecarboxylic acid and from α-cyano-3-phenoxy-benzyl alcohol, there was prepared the α-cyano-3-phenoxy-benzyl ester of the (±)-cis,trans-2,2-dimethyl-3-β-fluoro-β-trifluoromethyl-vinyl)-cyclopropanecarboxylic acid.

A partial separation of the geometrical isomers by chromatography on silica gel, as described in Example 1, has led to the following samples:
3-A: cis-isomer, purity ≧90% (NMR)
3-B: trans-isomer, purity ≧90% (NMR)
3-M: a mixture of isomers 3-A and 3-B in a ratio of about 3:5; refraction index $N_D^{25.5} = 1.5097$.

The NMR data of samples 3-A and 3-B have been recorded herebelow.

| | NMR (δ ppm)* |
|---|---|
| Compound 2-A | 1.2 (s, geminal methyls)<br>1.5–2 (m, $H_A$ c $H_B$)<br>2.2 (s, $CH_3$—C≡C)<br>3.8 (s, $CH_2$)<br>4.75 (s, $OCH_2$)<br>5.8 (s, $H_D$)<br>6.05 (dd, $H_C$)<br>7.1 (aromatic protons)<br>$J(H_C, H_A) = 8$ Hz<br>$J(H_C, F) = 33$ Hz |
| Compound 2-B | 1.15; 1.23 (s, geminal methyls)<br>1.57 (d, $H_B$)<br>2.27 (s, $CH_3$—C≡C)<br>2.27 (dd, $H_A$)<br>3.8 (s, $CH_2$)<br>4.75 (s, $OCH_2$)<br>5.2 (dd, $H_C$)<br>5.76 (s, $H_D$)<br>7.1 (aromatic protons)<br>$J(H_A, H_B) = 5$ Hz<br>$J(H_A, H_C) = 9$ Hz<br>$J(H_C, F) = 33$ Hz |

*s = singlet; d = doublet dd = doublet of doublet m = multiplet J = coupling constant

| | NMR (δ, ppm)* |
|---|---|
| compound 3-A | 1.8 + 2.35 (m, 2H, $H_A + H_B$)<br>5.9 (dd, 1H, Hc)<br>1.3 (s, 6H, geminal methyls)<br>6.22 (1H, CH—CN)<br>6.8 + 7.5 (m, 9H, aromatic protons)<br>$J(H_A - H_C) = 9$ Hz<br>$J(H_C - F_{trans}) = 31$ Hz |
| compound 3-B | 2.32 (dd, 1H, $H_A$)<br>1.7 (d, 1H, $H_B$)<br>5.23 (dd, 1H, $H_C$)<br>1.22 (s, 3H, $CH_3$)<br>1.32 (s, 3H, $CH_3$)<br>6.25 (d, 1H, CH—CN)<br>6.8 + 7.5 (m, 9H, aromatic protons)<br>$J(H_A - H_B) = 5$Hz<br>$J(H_A - H_C) = 9$Hz<br>$J(H_C - F_{trans}) = 32$ Hz |

*s = singlet; d = doublet; dd = doublet of doublet m = multiplet; J = coupling constant

EXAMPLE 4

By a process analogous to that described in Example 1, and starting from 2,2-dimethyl-3-trifluoromethylethynyl-cyclopropanecarboxylic acid and from α-cyano-3-phenoxy-benzyl alcohol, there was prepared α-cyano-3-phenoxy-benzyl ester of (±)-trans-2,2-dimethyl-3-trifluoromethylethynyl-cyclopropanecarboxylic acid whose NMR data have been recorded herebelow:

3-phenoxy-benzyl ester of the (±) cis,trans-2,2-dimethyl-3-(β-chloro-β-trifluoromethyl-vinyl)-cyclopropanecarboxylic acid.

A partial separation of the geometrical isomers by chromatography on silica gel, as described in Example 1, led to the following samples:

5-A: cis-isomer, purity≧90% (NMR)
5-B: trans-isomer, purity≧90% (NMR)
5-M: a mixture of isomers 5-A and 5-B, in a ratio of about 3:7; refraction index-$n_D^{26}$=1.5266.

The NMR data of samples 5-A and 5-B have been recorded herebelow.

| | NMR (δ, ppm)* |
|---|---|
| compound 5-A (CF$_3$—C(Cl)=, H$_c$, CH$_3$, CH$_3$, H$_A$, H$_B$, COO—CH$_2$—C$_6$H$_4$—O—C$_6$H$_5$) | 1.6–2.7 (m, 2H, H$_A$ + H$_B$)<br>1.22 (s, 6H, geminal methyls)<br>5.03 (s, 2H, CH$_2$)<br>6.7–7.5 (m, 10H, aromatic protons + H$_c$) |
| compound 5-B (CF$_3$—C(Cl)=, H$_c$, CH$_3$, CH$_3$, H$_B$, H$_A$, COO—CH$_2$—C$_6$H$_4$—O—C$_6$H$_5$) | 2.4 (dd, 1H, H$_A$)<br>1.8 (d, 1H, H$_B$)<br>5.82 ⎫ 2 duplets, 1H, Hc cis<br>6.1  ⎬ + trans on the double bond<br>1.20 (s, 3H, CH$_3$)<br>1.30 (s, 3H, CH$_3$)<br>5.08 (s, 2H, CH$_2$)<br>6.8–7.5 (m, 9H, aromatics)<br>$J_{(H_A-H_B)}$ = 5Hz<br>$J_{(H_A-H_C)}$ = 9Hz |

*s = singlet; d = doublet; dd = doublet of doublet; m = multiplet J = coupling constant

| | |
|---|---|
| Compound 4 (CF$_3$—C≡C, H$_3$C, CH$_3$, H$_B$, H$_A$, COO—CH(CN)—C$_6$H$_4$—OC$_6$H$_5$) | |
| NMR* (δ, ppm) | 1.83–2.2 (m, 2H, H$_A$ + H$_B$)<br>1.3 (s, 3H, CH$_3$)<br>1.35 (s, 3H, CH$_3$)<br>6.38 (s, 1H, CH—CN)<br>6.8–7.7 (m, 9H, aromatic protons) |

*s = singlet; m = multiplet

EXAMPLE 5

By a process analogous to that described in Example 1, and starting from 2,2-dimethyl-3-(β-chloro-β-trifluoromethyl-vinyl)cyclopropanecarboxylic acid and from 3-phenoxy-benzyl alcohol, there was prepared

EXAMPLE 6

By a process analogous to that described in Example 1, and starting from 2,2-dimethyl-3-(β-chloro-β-trifluoromethyl-vinyl)-cyclopropanecarboxylic acid and from α-cyano-3-phenoxy-benzyl alcohol, there was prepared the α-cyano-3-phenoxy-benzyl ester of the (±)-cis, trans-2,2-dimethyl-3-(β-chloro-β-trifluoromethyl-vinyl)-cyclopropanecarboxylic acid.

A partial separation of the geometrical isomers by chromatography on a silica gel column as described in Example 1, led to the following samples:

6-A: cis-isomer, purity≧90% (NMR)
6-B: E, trans-isomer, purity>90% (NMR)
6-M: a mixture of isomers 6-A and 6-B, in a ratio of about 3:7; refraction index-$n_D^{26}$=1.5256.

By an analogous preparation the mixture of isomers (E+Z)-trans was isolated. (Compound 6C)

The NMR data of sample 6-A, 6-B and 6C have been recorded herebelow.

| | NMR (δ, ppm)* |
|---|---|
| compound 6-A (CF$_3$—C(Cl)=, H$_c$, CH$_3$, CH$_3$, H$_A$, H$_B$, COO—CH(CN)—C$_6$H$_4$—O—C$_6$H$_5$) | 1.95–2.45 (m, 2H, H$_A$ + H$_B$)<br>1.3 (s, 6H, geminal methyls)<br>6.22 ⎫ (s, s, 1H, CH—CN)<br>6.28 ⎭<br>6.7–7.6 (m, 10H, aromatic protons + H$_c$) |

|  | NMR (δ, ppm)* |
|---|---|
| compound 6-B<br>Structure: CF₃/Cl-C=C-Hc/H₃C with cyclopropane ring bearing CH₃, H_B, H_A, COO-CH(CN)-C₆H₄-OC₆H₅ | 2.4 (d, d, 1H, H_A)<br>1.8 (d, 1H, H_B)<br>6.1 (d, 1H, H_C one single isomer)<br>1.2–1.37 (s, s, 6H, geminal methyls)<br>6.3 ⎫<br>6.37 ⎭ s, s, 1H, CH—CN)<br>6.8–7,6 (m, 9H, aromatic protons)<br>J (H_A − H_B) = 5Hz<br>J (H_A − H_C) = 9Hz |
| compound 6-C<br>Structure: CF₃—C(Cl)=C-Hc/H₃C with cyclopropane ring bearing CH₃, H_B, H_A, COO-CH(CN)-C₆H₄-O-C₆H₅ | 1.2–1.4 (6H, geminal methyls)<br>1.76 (d, 1H, H_B)<br>2.4 (dd, 1H, H_A)<br>5.7 (d) ⎫<br>6.08 (d) ⎭ (1H, H_c)<br>6.27 (1H, CH—CN)<br>6.8–7.55 (m, 9H, aromatic protons) |

*s = singlet, d = doublet, dd = doublet of doublet, m = multiplet, J = coupling constant

EXAMPLE 7

Following the same procedure as that described in Example 1, and starting from 2,2-dimethyl-3-(β-bromo-β-trifluoromethyl-vinyl)-cyclopropanecarboxylic acid and from 3-phenoxy-benzyl alcohol, there was prepared the 3-phenoxy-benzyl ester of (±)-cis,trans-2,2-dimethyl-3-(β-bromo-β-trifluoromethyl-vinyl)-cyclopropanecarboxylic acid.

A partial separation of the geometric isomers by means of chromatography on a silica gel column as described in Example 1, has led to the obtainment of the following samples:

7-B = trans-isomer, purity ≧ 90% (NMR),
7-M = mixture of cis-trans isomers in a ratio of about 1:1.2; $n_D^{24}$ = 1.5326

EXAMPLE 8

By a process analogous to that described in Example 1, starting from the 2,2-dimethyl-3-(β-bromo-β-trifluoromethyl-vinyl)-cyclopropanecarboxylic acid and from α-cyano-3-phenoxy-benzyl alcohol, there was prepared the α-cyano-3-phenoxy-benzyl ester of the (±)-cis,trans-2,2-dimethyl-3-(β-bromo-β-trifluoromethyl-vinyl)-cyclopropanecarboxylic acid. A partial separation of the geometrical isomers by chromatography on silica gel, as described in Example 1, led to the isolation of the following samples:

8-B: trans-isomer, purity ≧ 90% (NMR)
8-M: Mixture of cis-trans isomers in a ratio of about 1:1.2; refraction index-$n_D^{24}$ = 1.5310

|  | NMR (δ, ppm)* |
|---|---|
| Compound 7-B<br>Structure: F₃C—C(Br)=C-Hc/H₃C with cyclopropane ring bearing CH₃, H_B, H_A, COO-CH₂-C₆H₄-O-C₆H₅ | 2.25 (dd, 1H, H_A)<br>1.8 (d, 1H, H_B)<br>5.1 (s, 1H, H_c)<br>1.2 (s, 3H, CH₃)<br>1.3 (s, 3H, CH₃)<br>6.5 (d, 2H, CH₂)<br>6.8–7.55 (m, 9H, aromatic)<br>J(H_A − H_B) = 5 Hz<br>J(H_A − H_C) = 9 Hz |

*s = singlet; d = doublet; dd = doublet of doublet m = multiplet; J = coupling constant

|  | NMR (δ, ppm)* |
|---|---|
| Compound 8-B<br>Structure: CF₃—C(Br)=C-Hc/CH₃/CH₃ with cyclopropane ring bearing H_B, H_A, COO-CH(CN)-C₆H₄-O-C₆H₅ | 2.2–2.6 (m, 1H, H_A)<br>1.8 (d, 1H, H_B)<br>6.4 (2H, H_c + CH—CN)<br>1.2–1.33 (m, 6H, geminal methyls)<br>6.9–7.6 (m, 9H, aromatic protons)<br>J(H_A − H_B) = 5Hz<br>J(H_A − H_C) = 9 Hz |

*s = singlet; d = doublet; dd = doublet of doublet; m = multiplet; J = coupling constant

EXAMPLE 9

| (Compound 11-B) ($n_D^{25} = 1.5224$) | |
|---|---|
| | NMR ($\delta$, ppm)* |
| CF$_3$\\ /H$_C$ CH$_3$ CH$_3$<br>C=C<br>/ \\ \\ H$_B$<br>H$_D$ C———C CN<br>/ \\ \|<br>H$_A$ COO—CH—⬡<br>\|<br>O—C$_6$H$_5$<br>(Compound 11-B) | 1.15–1.3 (6H, geminal methyls)<br>1.75 (d, 1H, H$_B$)<br>2.1 (dd, 1H, H$_A$)<br>5.9 (m, 2H, H$_C$ + H$_D$)<br>6.3 (s, 1H, CH—CN)<br>7.1 (m, 9H, aromatic protons)<br>J (H$_A$ − H$_B$) = 5 Hz<br>J (H$_A$ − H$_C$) = 9 Hz |

*s = singlet, d = doublet, dd = doublet of doublet m = multiplet, J = coupling constant Following the same procedure as that described in Example 1 and starting from (±)trans-2,2-dimethyl-3-($\beta$-trifluoromethyl-Z-vinyl)-cyclopropanecarboxylic acid and 3-phenoxybenzyl alcohol, there was prepared 3-phenoxybenzyl ester of (±)-trans-2,2-dimethyl-3-($\beta$-triflouromethyl-Z-vinyl)cyclopropane carboxylic acid.

| (Compound 9-B) | |
|---|---|
| | NMR ($\delta$, ppm)* |
| H$_D$\\ H$_c$<br>C=C / H$_3$C CH$_3$<br>/ \\ /<br>CF$_3$ \\ H$_B$<br>H$_A$ COOCH$_2$—⬡<br>\|<br>O—C$_6$H$_5$<br>(Compound 9-B) | 2.45 (dd, 1H, H$_A$)<br>1.7 (d, 1H, H$_B$)<br>5.65 (m, 2H, H$_c$ + H$_s$)<br>1.23 (d, 6H, geminal methyls)<br>5.1 (s, 2H, CH$_2$)<br>6.8–7.6 (m, 9H, aromatic protons)<br>J (H$_A$ − H$_B$) = 5Hz |

*s = singlet; d = doublet; dd = doublet of doublet; m = multiplet; J = coupling constant

EXAMPLE 10

Following the same procedure as that described in Example 1 and starting from (±)-trans-2,2-dimethyl-3-($\beta$-trifluoromethyl-Z-vinyl)-cyclopropanecarboxylic acid and $\alpha$-cyano-3-phenoxybenzyl-alcohol, there was prepared $\alpha$-cyano-3-phenoxybenzyl ester of (±)-trans-2,2-dimethyl-3-($\beta$-trifluoromethyl-Z-vinyl)-cyclopropanecarboxylic acid.

| (Compound 10-B) | |
|---|---|
| | NMR ($\delta$, ppm)* |
| H$_D$\\ H<br>C=C / H$_3$C CH$_3$<br>/ \\<br>CF$_3$ H$_B$ CN<br>H$_A$ COO—CH—⬡<br>\|<br>O—C$_6$H$_5$<br>Compound 10-B | 2.45 (dd, 1H, H$_A$)<br>1.7 (d, 1H, H$_B$)<br>5.65 (m, 2H, H$_C$ + H$_D$)<br>1.23 (d, 6H, geminal methyls)<br>6.3 (s, 1H, CH—CN)<br>6.8–7.6 (m, 8H, aromatic protons)<br>J (H$_A$ − H$_B$) = 5 Hz |

*s = singlet, d = doublet, dd = doublet of doublets, m = multiplet, J = coupling constant

EXAMPLE 11

Following the same procedure as that described in Example 1 and starting from (±)-trans-2,2-dimethyl-3-($\beta$-trifluoromethyl-E-vinyl)-cyclopropanecarboxylic acid and $\alpha$-cyano-3-phenoxybenzyl alcohol, there was prepared $\alpha$-cyano-3-phenoxy-benzyl ester of (±)-trans-2,3-($\beta$-trifluoromethyl-E-vinyl)-cyclopropanecarboxylic acid.

EXAMPLE 12

Preparation of $\alpha$-cyano-3-phenoxybenzyl ester of (±)-cis,trans,2,2-dimethyl-3-(2-chloro-3,3,3-trifluoropropyl)-cyclopropanecarboxylic acid (Compound 12). A solution of 3 g of (±)-cis,trans-2,2-dimethyl-3-(2-chloro-3,3,3-trifluoropropyl)-cyclopropanecarboxylic acid chloride (obtained from the corresponding ethyl ester by hydrolysis and reaction with SOCl$_2$) in 50 ml anhydrous benzene, was admixed to a solution of 2.9 g of $\alpha$-cyano-3-phenoxybenzyl alcohol in 50 ml of anhydrous benzene.

2 ml of pyridine were added to the resulting solution which was then kept at room temperature for 24 hours. Then the solution was washed with water until a neutral pH was attained. The organic phase was separated and dried, then the solvent was evaporated under vacuum. Thereby were obtained 5.1 g of the desired product as a yellow viscous oil (Refraction index $n_D^{24} = 1.5125$, elemental analysis and IR spectroscopic data consistent with the assigned structure).

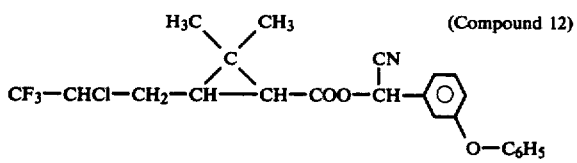
(Compound 12)

EXAMPLE 13

Preparation of 3-phenoxybenzyl ester of (±)-cis, trans-2,2-dimethyl-3-(2-chloro-3,3,3-trifluoropropyl)-cyclopropanecarboxylic acid (Compound 13).

Following the procedure described in Example 12 and by reacting 3 g of (±)-cis,trans-2,2-dimethyl-3-(2-chloro-3,3,3-trifluoropropyl)-cyclopropanecarboxylic acid chloride with 3-phenoxybenzyl alcohol, 5 g of the desired product were obtained in form of a viscous colorless oil (Refraction index $n_D{}^{23}=1.5160$, IR spectroscopic data consistent with the assigned structure).

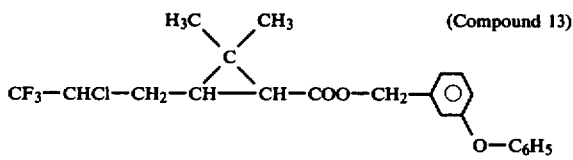
(Compound 13)

The product thus obtained was then chromatographed on a silica gel column using a mixture of n hexane-diethyl ether (95:5) as eluant.
Two samples were collected:
13-A, cis isomer, $n_D{}^{24}=1.5169$
13-B, trans isomer, $n_D{}^{24}=1.5171$

EXAMPLE 14

Preparation of α-cyano-3-phenoxybenzyl ester of (±)-cis, trans-2,2-dimethyl-3-(2,2-dibromo-3,3,3-trifluoropropyl)-cyclopropanecarboxylic acid (Compound 14).

Following the procedure described in Example 12 and by reacting 3 g of (±)-cis,trans-2,2-dimethyl-3-(2,2-dibromo-3,3,3-trifluoropropyl)-cyclopropanecarboxylic acid chloride with α-cyano-3-phenoxybenzylalcohol, 4.5 g of the desired product were obtained in form of a viscous oil (Elemental analysis and IR spectroscopic data consistent with the assigned structure)

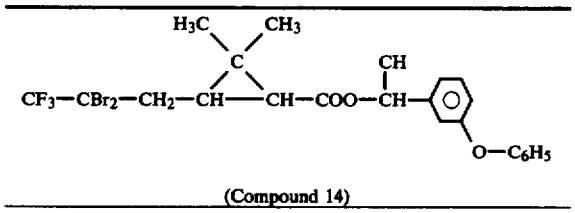

| (Compound 14) |
|---|
| NMR (δ, ppm)* |
| 1.2–2.7 (10H, protons of the acylic moiety) |
| 6.3 (s, 1H, CH—CN) |
| 6.7–7.6 (m, 9H, aromatic protons) |

*NMR = Nuclear Magnetic Resonance spectroscopic data s = singlet, m = multiplet.

EXAMPLE 15

Insecticide activity of the compounds of the invention

The compounds of this invention have been tested on larvae and on adults of the following species of phytophagouses, following the methods indicated hereunder (the data have been recorded on Table 2).

(A) Biological activity on *Macrosiphum euphorbiae* (aphides)

Small potato plants grown in pots have been infested with adult females of aphides and, after a few hours, were then besprinkled with an aqueous dispersion of the products under examination (see Table 2). The mortality percentage was evaluated 24 hours after the treatment (mortality of aphides on untreated plants=0).

(B) Biological activity on *Pieris brassicae* (lepydoptera)

Cut-off cauliflower leaves were subjected to besprinkling with an aqueous dispersion of the products under examination (see Table 2). After drying, the leaves were infested with 5 days old larvae. The mortality percentage of the larvae (mortality on untreated leaves=0) was determined 48 hours after the treatment.

(C) Biological activity on *Leptinotarsa decemlineata* (Coleoptera)

Small potato plants grown in pots were infested with 4 days old larvae, and then submitted to besprinkling with an aqueous dispersion of the products under examination (see Table 2). The mortality percentage (mortality on untreated plants=0) was determined 48 hours after treatment.

(D) Biological activity on *Culex Pipiens* adults (Dyptera)

Rectangular strips of Whatman paper No. 1 were treated uniformly with an acetonic solution of the products under examination (see Table 2).

After evaporation of the solvent, the inside or internal part of a perspex cylinder (model OMS) was lined with each treated paper and closed with a net. There were then introduced into the cylinder 2-3 days old females. After one hour from the start of the contact, the insects were transferred to an identical cylinder likewise lined with untreated paper and fed with a sugary solution. The mortality percentage (mortality of untreated insects=0) was determined after 24 hours from the beginning of the treatment.

(E) Biological activity on *Blatta orientalis* (Ortoptera)

The bottom and walls of glass crystallizers (cylinders) were treated uniformly with an acetonic solution of the products under examination (see Table 2). After evaporation of the solvent, in each crystallizer there were introduced 80–100 days old neanides, after which the crystallizers were closed with a metal net cover. Twenty-four hours after the starting of the treatment the insects were transferred into similar, untreated crystallizers and were properly nourished. The mortality percentage (mortality of untreated insects=0) was determined 48 hours after the start of the treatment.

(F) Biological activity of adults of *Tetranychus urticae* (Acari)

Discoids of leaves of bean plants were infested with acarus adults and successively besprinkled with an aqueous dispersion of the products under examination (see Table 2). The mortality percentage was determined 24 hours after the treatment (mortality of acari on untreated discoids=0).

17

(G) Biological activity on *Musca domestica* (Dyptera)

4 days old adults were treated, by topical application by a micro syringe, with an acetonic solution of the products under examination (see Table 2). The mortality percentage (mortality of insects treated only with acetone=0) was determined 24 hours after treatment.

18

EXAMPLE 17

Activity and action persistence test on acari in the open field

The test was conducted in the open field in order to test the activity and action persistence of a number of representative compounds against acari (*Tetranychus*

TABLE 2

| | Insecticide and acaricide activity (expressed as mortality percentage at the indicated doses) | | | | | | | | | | | | | |
|---|---|---|---|---|---|---|---|---|---|---|---|---|---|---|
| | Macrosiphum E | | Pieris B | | Leptinotarsa D | | Musca D | | Culex P.(ad) | | Blatta O. | | Tetracyclus U.(ad.) | |
| | dose ($X_o$) | mort. (X) | dose ($X_o$) | mort. (X) | dose ($X_o$) | mort. (X) | dose ($\gamma$/ino.) | mort. (X) | dose ($g/m^2$) | mort. (X) | dose ($g/m^2$) | mort. (X) | dose ($X_o$) | mort. (X) |
| 1-A | 0.01 | 100 | | | 0.01 | 100 | 0.05 | 100 | 0.2 | 100 | 0.1 | 100 | 0.1 | 100 |
| | 0.005 | 100 | 0.005 | 100 | | | 0.01 | 100 | | | 0.01 | 100 | | |
| | | | 0.001 | 100 | | | | | | | | | | |
| 1-B | | | | | | | 0.05 | 100 | 0.2 | 57 | 0.1 | 100 | 0.1 | 90 |
| | 0.01 | 100 | | | 0.01 | 100 | 0.01 | 82 | | | 0.01 | 65 | | |
| | 0.005 | 100 | 0.005 | 100 | | | | | | | | | | |
| | | | 0.001 | 95 | | | | | | | | | | |
| 1-M | | | | | | | 0.05 | 100 | 0.2 | 100 | 0.1 | 100 | 0.1 | 86 |
| | 0.01 | 100 | | | 0.01 | 100 | 0.01 | 80 | | | 0.01 | 100 | | |
| | 0.005 | 100 | 0.005 | 100 | | | | | | | | | | |
| | | | 0.001 | 100 | | | | | | | | | | |
| 2-A | 0.01 | 100 | | | 0.01 | 35 | 0.05 | 100 | 0.2 | 100 | 0.1 | 100 | 0.1 | 60 |
| | 0.005 | 91 | 0.005 | 100 | | | 0.01 | 90 | | | 0.01 | 100 | | |
| | | | 0.001 | 50 | | | | | | | | | | |
| 2-B | 0.01 | 100 | | | 0.01 | 85 | 0.05 | 92 | 0.2 | 50 | 0.1 | 80 | 0.1 | 37 |
| | 0.005 | 93 | 0.005 | 55 | | | | | | | | | | |
| 3-A | 0.005 | 100 | 0.005 | 100 | 0.01 | 100 | 0.01 | 100 | 0.2 | 100 | 0.01 | 100 | 0.1 | 100 |
| 3-B | 0.005 | 100 | 0.005 | 100 | 0.01 | 100 | 0.01 | 100 | 0.2 | 100 | 0.01 | 10 | 0.1 | 100 |
| | | | 0.001 | 100 | | | | | | | | | | |
| 3-M | 0.005 | 100 | 0.005 | 100 | 0.01 | 100 | 0.05 | 100 | 0.2 | 100 | 0.01 | 100 | 0.1 | 81 |
| | | | | | | | 0.01 | 100 | | | | | | |
| 4 | 0.01 | 100 | 0.005 | 100 | 0.01 | 100 | 0.05 | 100 | 0.2 | 44 | 0.01 | 100 | 0.1 | 100 |
| | 0.005 | 76 | | | | | | | | | | | | |
| 9-B | 0.01 | 60 | 0.005 | 100 | 0.01 | 10 | 0.05 | 100 | 0.2 | 100 | | | 0.1 | 40 |
| 10-B | 0.01 | 100 | 0.005 | 100 | 0.01 | 100 | 0.05 | 100 | 0.2 | 100 | | | 0.1 | 80 |
| | | | 0.001 | 100 | | | | | | | | | | |
| Phenothrin (reference compound) | 0.01 | 53 | 0.005 | 0 | 0.01 | 0 | 0.05 | 70 | 0.2 | 0 | | | 0.1 | 0 |
| Permethrin (reference compound) | | | | | | | 0.05 | 100 | 0.2 | 28 | 0.1 | 100 | 0.1 | 47 |
| | 0.01 | 100 | | | 0.01 | 77 | 0.01 | 32 | | | 0.01 | 77 | | |
| | 0.005 | 96 | 0.005 | 100 | | | | | | | | | | |
| | | | 0.001 | 83 | | | | | | | | | | |

EXAMPLE 16

Acute toxicity on rats by oral administering

Animal under test: albino mouse; Wistar stock, 50% males and 50% females.

The animals, after a stalling period, were kept fasting from 6 hours before to 2 hours after the treatment and were successively kept under observation for 14 days, during which they were fed with calibrated fodder in pellets and water libitum. The treatment was carried out by introducing into the stomach of the animals established quantities of the product through a gastric probe connected to a precision syringe.

During the whole period of observation the mortality and all possible symptoms of intoxication were recorded.

Compound 1-B was tested on rats according to the above specified methodology, in a dose of 200 mg of active substance/kg of live weight, without observing any mortality of the test animals after the test.

*urticae*) resisting the commonly used insecticides.

The compounds were applied in the form of an hydroacetonic dispersion with the addition of a wetting agent ("Fitofil" Montedison in a $0.5°/_{oo}$ concentration) nebulizing them uniformly on the cultivation up to the limit of dripping. (Concentration of the active principle = $0.3°/_{oo}$).

Data were recorded at time intervals from the start of the treatment, by counting the number of adult acari present on suitably sampled leaves.

It is well known that under the above specified conditions all the pyrethroids listed in Table 1, with the exception of Permethrin, Cypermethrin and Decamethrin, undergo a fast decay becoming totally inactive after a very short period of time.

From our tests it turned out that Permethrin and Cypermethrin become totally inactive after 14 days. On the contrary, compounds of the present invention showed still a remarkable activity after the same period of time.

We claim:

1. A compound of the formula

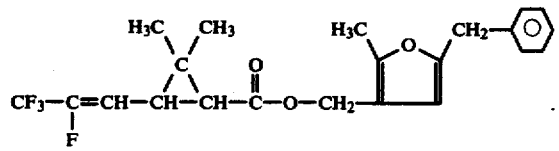

2. A compound according to claim 1, which is the 2-methyl-5-benzyl-3-furylmethyl ester of (±)-cis,trans-2,2-dimethyl-3-(β-fluoro-β-trifluoromethyl-vinyl)-cyclopropanecarboxylic acid.

3. A compound according to claim 1, which is the 2-methyl-5-benzyl-3-furylmethyl ester of (±)-cis-2,2-dimethyl-3-(β-fluoro-β-trifluoromethyl-vinyl)-cyclopropanecarboxylic acid.

4. A compound according to claim 1, which is the 2-methyl-5-benzyl-3-furylmethyl ester of (±)-trans-2,2-dimethyl-3-(β-fluoro-β-fluoromethyl-vinyl)-cyclopropanecarboxylic acid.

5. An insecticidal and acaricidal composition comprising an effective amount of one or more of the compounds of claim 1 in association with an inert carrier.

6. A method for fighting infestations by insects and acari, comprising distributing in the zone to be protected an effective amount of one or more of the compounds of claim 1.

7. The method of claim 6, in which the effective amounts of the compound or compounds is present in a composition in association with an inert carrier.

* * * * *